United States Patent [19]

David et al.

[11] Patent Number: 5,594,150

[45] Date of Patent: Jan. 14, 1997

[54] PROCESS FOR THE PREPARATION OF A SECONDARY OR TERTIARY HYDROXYLATED AMINE COMPOUND FROM A PRIMARY OR SECONDARY AMINE COMPOUND AND A PRODUCT MADE BY THE PROCESS

[75] Inventors: Catherine David, Antony; Gilles Teral, Paris; Henry Ledon, Versailles; Jean-Pierre Boiteux, Saix, all of France

[73] Assignee: Chemoxal S.A., Paris, France

[21] Appl. No.: 268,530

[22] Filed: Jul. 6, 1994

[30] Foreign Application Priority Data

Jul. 6, 1993 [FR] France ................................. 93 08245

[51] Int. Cl.$^6$ ...................... C07D 233/72; C07C 205/27
[52] U.S. Cl. ..................... 548/573; 545/574; 562/567; 562/569; 564/475; 564/477
[58] Field of Search ..................... 548/573, 574; 562/567, 569; 564/475, 477

[56] References Cited

U.S. PATENT DOCUMENTS

| 3,647,868 | 3/1972 | Ernst . | |
|---|---|---|---|
| 3,754,003 | 8/1973 | Pedrazzoli et al. | 548/574 X |
| 3,954,873 | 5/1976 | Gipson | 564/477 X |
| 4,060,613 | 11/1977 | Ferland et al. | 548/573 X |
| 4,112,231 | 9/1978 | Weibull et al. | 544/174 |
| 4,201,725 | 5/1980 | Pigerol et al. | 564/477 X |
| 4,223,138 | 9/1980 | Schubart | 544/162 |
| 4,281,201 | 7/1981 | Abend | 564/506 |
| 4,321,271 | 3/1982 | McDonald | 564/477 X |

FOREIGN PATENT DOCUMENTS

| 2099030 | 3/1972 | France . |
| 2128331 | 10/1972 | France . |
| 2515645 | 5/1983 | France . |

OTHER PUBLICATIONS

Fette, Seifen, Anstrichmittel, vol. 84, No. 3, 1982, pp. 87–92 (Rutzen).

*Primary Examiner*—Floyd D. Higel
*Attorney, Agent, or Firm*—Burns, Doane, Swecker & Mathis, L.L.P.

[57] ABSTRACT

Process for the preparation of a hydroxylated secondary or tertiary amine compound having a hydroxyl function β to the amine function, according to which a primary or secondary amine compound is reacted with a compound containing an epoxy function in the presence of a phase transfer catalyst.

35 Claims, No Drawings

5,594,150

PROCESS FOR THE PREPARATION OF A SECONDARY OR TERTIARY HYDROXYLATED AMINE COMPOUND FROM A PRIMARY OR SECONDARY AMINE COMPOUND AND A PRODUCT MADE BY THE PROCESS

BACKGROUND OF THE INVENTION (i) Field of the Invention

The present invention relates to a new process for the preparation of a hydroxylated secondary or tertiary amine compound starting, respectively, from a primary or secondary amine compound, which does not require the employment of an organic solvent such as alcohols or ketones.

(ii) Description of the Related Art

It is known to prepare hydroxylated secondary or tertiary amine compounds, containing a hydroxyl group β to the amine group, by having a primary or secondary amine compound, respectively, react with an epoxy compound, in an organic solvent medium, generally comprising an alcohol or a ketone.

The compounds thus formed give rise to the disadvantage in that they contain traces of organic solvent from the process, making them ill-suited for use in cosmetics, pharmaceuticals, or in any products where the absence of an organic solvent is a requirement.

French Patent 2,099,030 describes a process for the preparation of a compound N-(hydroxyhydrocarbyl)-N-(alkylaminocarboxylate) by reaction between a 1,2-epoxide of hydrocarbide compound and an N-substituted aminocarboxylic acid, in an aqueous medium, optionally in the presence of an alcohol.

However, in order to obtain acceptable yields, this reaction must be carried out in a reactor under very strong agitation, in a manner which is incompatible with implementation on an industrial scale.

In addition, French Patent 2,099,030 recommends purifying the resulting product of the reaction by treating it with an organic solvent medium brought to reflux. It is understood that such purification method leads to the obtaining of a product which cannot be made free of organic solvent and, besides, the employment of a solvent brought to reflux conditions gives rise to significant risks relating to the safety of persons.

Besides, H. Rutzen in Fette, Seifen, Anstrichmittel, Vol. 84, No. 3, 1982, Hamburg, pages 87–92, "Quaterernierung von tertiären Aminsalzen mit langkettigen Epoxiden" describes a process for the preparation of quaternary ammonium compounds by reaction of a tertiary amine compound with a compound containing an epoxy function, in the presence of a phase transfer catalyst.

SUMMARY AND OBJECTS OF THE INVENTION

The present invention has as its principal object a process for the preparation of a hydroxylated secondary or tertiary amine compound, which can be employed in the absence of an organic solvent and, which can be carried out with agitation speeds which are compatible with existing industrial reactors.

The present invention thus relates to a process for the preparation of a hydroxylated secondary or tertiary amine compound having a hydroxyl function group β to the amine group starting from, respectively, a primary or secondary amine compound, comprising reacting the primary or secondary amine compound with an epoxy compound in the presence of (i) a phase transfer catalyst and (ii) a mineral base then, if necessary, the hydroxylated secondary or tertiary amine compound which is formed from the phase transfer catalyst is separated.

In a second aspect, the present invention relates to a composition comprising:

(i) at least one hydroxylated secondary or tertiary amine compound having a hydroxyl β to the amine; and (ii) a phase transfer catalyst, the composition being substantially free of organic solvents.

With the foregoing and other objects, advantages and features of the invention that will become hereinafter apparent, the nature of the invention may be more clearly understood by reference to the following detailed description of the invention and to the appended claims.

DETAILED DESCRIPTION OF PREFERRED EMBODIMENTS,

It has in effect been observed that the presence of a phase transfer catalyst in the reaction medium permitted the resolution of the problems expounded upon above. However, it is essential to carry out the reaction in the presence of a mineral base, at least when the primary or secondary amine is in a free form, such in order to obtain a suitable yield.

In the context of the present invention, a phase transfer catalyst is a chemical compound permitting the reaction between two chemical entities which are found in different phases such as, for example, two liquid entities of different nature.

Advantageously, the primary or secondary amine compound contains at least one oxygen-containing group which can be formed into a salt such as the groups —COO$^-$, —SO$_3^{3}$, —PO$_4$H$^-$, —SO$_4^{-2}$ or —PO$_3^{2-}$, the groups essentially being in a free or salt form. It should be understood that by free form, it is meant that the oxygen-containing group capable of forming a salt has a counter-ion H$^+$, and by salt form is meant that the counter-ion consists of an organic or mineral cation, such as 4 or a cation of an NH$_4^+$ alkaline or alkaline earth metal, such as sodium, potassium or calcium.

More particularly, the primary or secondary amine compound can consist of a carboxyamino compound containing one or two carboxylic groups in free or salt form.

Such carboxyamino compounds can notably consist of amino acids, oligopeptides, peptides, N-acylated amino acids, N-acyl oligopeptides, mono or polycyclic heterocyclic carboxyamino compounds containing from 3 to 14 carbon atoms and at least one nitrogen atom as the heteroatom, or mixtures of these carboxyamino compounds.

The amino acids can consist of α-amino acids such as sarcosine, asparagine, valine, leucine, isoleucine, threonine, methionine, phenylalanine, tryptophane, lysine, hydroxylysine, alanine, arginine, aspartic acid, cystine, cysteine, glutamic acid, glycine, histidine, proline, hydroxyproline, serine, tyrosine, glutamine, or mixtures of these amino acids.

These amino acids can be present under the D form or, preferably, under the L form or the D, L form.

The N-acylated amino acids and the N-acyl oligopeptides mentioned above are well known. They can notably be prepared according to the processes described in French Patent 2,619,711 or in patent application JP-03/294298.

The heterocyclic carboxyamino compounds which can be employed in the process of the invention can contain, besides a nitrogen heteroatom, from 1 to 3 other heteroatoms chosen among N, O and S. Compounds of such type can consist of carboxylic derivatives of morpholine, pyridine, pyrazine, pyrimidine, purine, quinoleine, and isolquinoleine, of imidazole, pyrazole, thiazole, or oxazole or a compound such as nicotinic acid. A primary or secondary amine compound including a group —SO$_3^-$ can consist of taurine or methyltaurine.

As the primary or secondary amine which can be used as the starting product in the process according to the present invention, there can be mentioned compounds such as chitine or those of the formula (I):

in which R is hydrogen or a $C_1$–$C_{30}$ radical and G is the residue of a monosaccharide, a disaccharide, a polysaccharide or hexitol.

Preferably R is hydrogen or a $C_1$–$C_4$ alkyl radical.

G can be a monosaccharide such as galactose, fructose, glucose, mannose, xylose, arabinose, lyxose, ribose or ribulose, of a disaccharide such as saccharose, maltose, or lactose, a polysaccharide such as cellulose or starch or hexitol, such as sorbitol, mannitol or galactitol.

The preferred compounds of formula (I) consist of glucamine, N-methylglucamine and glycosamine.

It should be understood that one of the primary or secondary amine compounds described above, or mixtures of these, can be employed.

An epoxy compound which can be employed in the process according to the invention can consist of a compound of formula (II):

in which the substituents $R_1$, $R_2$, $R_3$, and $R_4$, which may be identical or different, are:

(i) hydrogen (ii) a group $R_5[(CH_2)_8X]_t$, $R_5$ being a linear or branch, saturated or unsaturated, aliphatic radical containing from 1 to 30 carbon atoms, a cycloaliphatic radical containing from 3 to 12 carbon atoms or an aryl radical, $R_5$ optionally having one to three hydroxyl or amine groups or (iii) a group $R_6COOR_7$, where $R_6$ is a $C_1$–$C_{10}$ alkylene radical or $R_6$ represents a covalent bond and $R_7$ is H or a saturated or unsaturated, linear or branched aliphatic radical containing from 1 to 30 carbon atoms, preferably from 1–4 carbon atoms.

X is hydrogen or sulfur, s is equal to 0 or ranges between 1 and 4 and t is equal to 0 or ranges between 1 and 20, with the proviso that at least one of $R_1$, $R_2$, $R_3$ and $R_4$ is different from hydrogen.

Advantageously three of the substituents $R_1$, $R_2$, $R_3$ and $R_4$ represent hydrogen, the fourth of these substituents being different from hydrogen; more particularly the last substituent can be a $C_1$–$C_{20}$ alkyl radical, preferably $C_8$–$C_{14}$.

The phase transfer catalysts employed can be those described in W. P. Weber, G. W. Gorel "Phase Transfer Catalysis in Organic Synthesis"—Springer-Verlag, Berlin, Heidelberg, New-York (1977); C. M. Starks, C. Liotta "Phase Transfer Catalysis. Principles and Techniques"—Academic Press, New York, San Francisco, London (1978); or E. V. Dehmlow, E. S. Dehmlow "Phase Transfer Catalysis"—VCH Verlagsgesellschaft, Weinheim (1980 and 1983).

Preferably, the phase transfer catalyst is a quaternary ammonium compound, such as a halide of a quaternary ammonium compound, such as the bromides and chlorides of tetralkylammonium or of trialkylaryl-ammonium. Such compounds can more particularly consist of didodecyldimethyl-ammonium bromide, trioctylmethylammonium chloride or dodecyldimethylbenzyl-ammonium bromide. The phase transfer catalyst can also be an organic derivative of phosphonium ion, such as the halides of tetralkyl phosphonium, tetra-aryl phosphonium or triarylalkyl phosphonium. Such compounds notably can consist of bromides or chlorides of tetrabutyl phosphonium, tetraphenyl phosphonium, triphenylmethyl phosphonium or tetrabutyl phosphonium.

The reaction between the primary or secondary amine compound and the expoxy compound can optionally be carried out in the presence of a solvent, which solvent consists preferably of water, for example water in which the primary or secondary amine compound can be dissolved. The concentration of the primary or secondary amine compound in the reaction medium can range between 0.5 and 60 moles/liter, preferably between 1 and 20 moles/liter.

In the course of the reaction, the water which is formed can be continuously eliminated.

Advantageously, the reaction is carried out in the presence of a mineral base chosen from among LiOH, $Na_2CO_3$, $NaHCO_3$, $KHCO_3$, $K_2CO_3$, $NH_4OH$, or, preferably, NaOH or KOH.

The molar ratio between the primary or secondary amine compound and the base ranges typically between 0.5 and 5 and, preferably, is on the order of about 1.

The molar ratio between the compound containing a hydroxy function and the primary or secondary amine compound can range between 0.5 and 10, and preferably between 0.8 and 1.20.

The weight content of the phase transfer catalyst employed generally ranges between 0.1 and 10% by weight of the primary or secondary amine compound.

The reaction between the epoxy compound and the primary or secondary amine compound can be carried out at a temperature greater than 90° C., preferably at a temperature ranging between 95° C. and 160° C., more preferably ranging between 95° and 125° C. This reaction is generally carried out at atmospheric pressure or a temperature which is close to atmospheric pressure. The agitation speed of the reaction medium which is generally employed is less than 1000 rpm, preferably ranging between 500 and 50 rpm.

At the end of the reaction between the primary or secondary amine epoxy compound and the compound, there is obtained a hydroxylated secondary or tertiary amine compound having a hydroxyl group which is β to the amine group in admixture with the phase transfer catalyst. If it is desired to obtain solely the hydroxylated compound, the phase transfer catalyst can be eliminated according to classical methods, well known to persons skilled in the art.

The hydroxylated secondary or tertiary amine compound obtained can be a compound of the formula (III):

a compound of formula (IV):

or a mixture of the compounds of formulas (III) and (IV).

In the formulas (III) and (IV), $R_1$, $R_2$, $R_3$ and $R_4$, which are identical or different, are as defined above, with the proviso that in the formula (III), one of $R_1$ and $R_2$ is different from hydrogen and in the formula (IV), one of $R_3$ and $R_4$ is different from hydrogen, $R_8$ and $R_9$, which may be identical or different, are:

One of the meanings of $R_1$ given above a group $R_{10}$–ZM, where $R_{10}$ is a linear or branched, saturated or unsaturated aliphatic radical or an aryl radical, Z is an oxygen-containing group capable of forming a salt such as —COO$^-$, —SO$_3^-$, or —PO$_3^{2-}$, —SO$_4^{-2}$ or HPO$_4^-$ and M is a counter-ion, such as NH$_4^+$ or a cation of an alkali or alkaline earth metal, a residue of a monosaccharide, a disaccharide, a polysaccharide or hexitol such as those defined above, a group

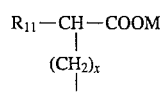

where $R_{11}$ is the rest of an amino acid, an oligopeptide or a peptide, M has the meaning given above and x is 0 or an integer ranging between 1 and 5 or $R_8$ and $R_9$ together with the nitrogen atom to which they are bound, form a monocyclic or polycyclic heterocycle containing from 3 to 14 carbon atoms and, if necessary, 1 to 3 additional heteroatoms chosen among O, S and N, the heterocycle optionally being substituted by 1 or 3 carboxylic and/or hydroxyl functions.

According to another aspect, the invention relates to a composition containing at least a secondary or tertiary hydroxylated amine compound having a hydroxyl β from the amine and a phase transfer catalyst, the composition being substantially free of organic solvents such as alcohols and ketones.

A preferred hydroxyl compound can consist of a compound of formula (III), a compound of formula (IV) such as defined above, or a mixture of these. Advantageously, the phase transfer catalyst included in the composition is an organic derivative of phosphonium ion or a quaternary ammonium compound and, preferably, a halide of a quaternary ammonium compound, such as defined above.

The weight ratio between the phase transfer catalyst and the hydroxyl compound present in the composition according to the invention can range between 0.001 and 0.1, preferably between 0.001 and 0.05.

Such a composition can be prepared according to the process of the invention described above, it being understood that the stage of separation between the hydroxylated secondary or tertiary amine compound not being carried out.

To the extent that the composition according to the invention, such as defined above, is free from organic solvent, it can advantageously be employed as a tensio active agent, notably in cosmetic, pharmaceutical, hygienic or food compositions. Such a composition can also be used as a detergent agent.

The examples which follow have as their object the illustration of the present invention.

In the examples, there was employed as the phase transfer catalyst AMONYL®Br 1244 which is dodecyldimethylbenzylammonium bromide, and ALIQUAT®336 which is trioctylmethylammonium chloride.

EXAMPLE 1

In a 100 ml reactor topped by a Dean Stark, itself topped by a refrigerant and characterized by a mechanical agitation with the aid of an anchor blade (500 rpm), there was introduced 3.08 g of potassium hydroxide in tablets (55 mmoles) and 10 ml of distilled water. The reaction mixture was cooled to 5° C. and there was added, in fractions, 4.90 g of sarcosine (55 mmoles). The mixture was agitated for 15 minutes while allowing the temperature to climb to 20° C. There was then added 0.3 g of AMONYL®Br1244 (6% mass/mass of sarcosine) and the mixture was again agitated at 500 rpm for 15 minutes at 20° C. 10.0 g of epoxydodecane (55 mmoles) were added. The crude reaction mixture was heated to 100° C. for 8 hours and cooled to 20° C.

The N-(2'-hydroxydodecyl) sarcosinate of potassium was obtained with 86% yield.

By way of comparison, the above test was reproduced without the phase transfer catalyst. The expected product could be synthesized with a yield of only 74%.

By way of comparison, the above test was again reproduced, but this time in the absence of potassium hydroxide. The detected reaction product was obtained with a yield of less than 7%.

EXAMPLE 2

In a reactor identical to that of Example 1, there was introduced under agitation 3.08 g of potassium hydroxide in tablets (55 mmoles) and 10 ml of distilled water. The reaction mixture was cooled to 5° C. and then there was added, in fractions, 4.90 g of sarcosine (55 mmoles). The mixture was agitated for 15 minutes while letting the temperature climb to 20° C. There was then added 0.02 g of ALIQUAT®336 (0.4% mass/mass of Sarcosine) and agitation was again commenced at 500 rpm for 15 minutes at 20° C. There was then added 10.0 g of epoxydodecane (55 mmoles). The crude reaction mixture was heated to 100° C. for 8 hours and cooled to 20° C.

The N-(2'-hydroxydodecyl) sarcosinate of potassium was obtained with yield of 87%.

EXAMPLE 3

In a reactor identical to that of Example 1, there was introduced under agitation 456 mg of sodium hydroxide in tablets (11 mmoles) and 1 ml of distilled water. The reaction mixture was cooled to 5° C. and there was added, in fractions, 1.02 g of sarcosine (11 mmoles). The mixture was agitated for 15 minutes while letting the temperature climb to 20° C. There was then added 51 mg of ALIQUAT®336 (0.5% mass/mass of Sarcosine) and the mixture was agitated again at 500 rpm for 15 minutes at 20° C. There was then added 2.10 g of epoxydodecane (11 mmoles). The crude reaction mixture was heated to 100° C. for 8 hours and cooled to 20° C.

The N-(2'-hydroxydodecyl) sarcosinate of sodium was obtained at a yield of 85%.

EXAMPLE 4

In a reactor identical to that of Example 1, there was introduced under agitation 3.08 g of potassium hydroxide in tablets (55 mmoles) and 1 ml of distilled water. The reaction mixture was cooled to 5° C. and there was added, in fractions, 4.90 g of Sarcosine (55 mmoles). The mixture was agitated for 15 minutes while allowing the temperature to climb to 20° C. There was then added 0.3 g of ALIQUAT®336 (6% mass/mass of Sarcosine) and the mixture as agitated once again at 500 rpm for 15 minutes at 20° C. There were then added 10.0 g of epoxydodecane (55 mmoles). The crude reaction mixture was heated to 100° C. for 8 hours and cooled to 20° C.

The N-(2'-hydroxydodecyl) sarcosinate of potassium was obtained at a yield of 97%.

By way of comparison, the above-described test was repeated without the phase transfer catalyst. A yield of 78% was obtained.

EXAMPLE 5

In a reactor identical to that of Example 1, there was introduced under agitation 3.08 g of potassium hydroxide in tablets (55 mmoles) and 10 ml of distilled water. The reaction mixture was cooled to 5° C. and there was added, in fractions, 6.40 g of proline (55 mmoles). The mixture was agitated for 15 minutes while allowing the temperature to climb to 20° C. There was then added 0.3 g of ALIQUAT®336 (6% mass/mass of Proline) and the mixture was agitated once again at 500 rpm for 15 minutes at 20° C. There was then added 10.0 g epoxydodecane (55 mmoles). The crude reaction mixture was heated to 100° C. for 8 hours and cooled to 20° C.

The N-(2'-hydroxydodecyl) prolinate of potassium was obtained with a yield of 98%.

EXAMPLE 6

In a reactor identical to that of Example 1, there was introduced under agitation 3.08 g of potassium hydroxide in tablets (55 mmoles) and 10 ml of distilled water. The reaction mixture was cooled to 5° C. and there was added, in fractions, 6.04 g of D, L-threonine (55 mmoles). The mixture was agitated for 15 minutes while allowing the temperature to climb to 20° C. There was then added 0.3 g of ALIQUAT®336 (5% mass/mass of D,L-threonine) and the mixture was once again agitated at 500 rpm for 15 minutes at 20° C. There was then added 10.0 g of epoxydodecane (55 mmoles). The crude reaction mixture was heated to 100° C. for 8 hours and cooled to 20° C.

The N-(2'-hydroxydodecyl) D,L-threoninate of potassium was obtained with an 81% yield.

By way of comparison, this test was reproduced without the phase transfer catalyst. No condensation product was formed. Two limpid phases were observed, one containing the epoxyalkane and the other containing the amino acid.

By way of comparison, the above test was again reproduced, but this time without the addition of potassium hydroxide. No reaction product was detected.

EXAMPLE 7

In a reactor identical to that of Example 1, there was introduced under agitation 3.08 g of potassium hydroxide in tablets (55 mmoles) and 10 ml of distilled water. The reaction mixture was cooled to 5° C. and there was added, in fractions, 8.50 g of L-histidine (55 mmoles). The mixture was agitated for 15 minutes while allow the temperature to climb to 20° C. There was added 0.3 g of ALIQUAT®336 (3.5% mass/mass of L-histidine) and the mixture was again agitated at 500 rpm for 15 minutes at 20° C. There was then added 10.0 g of epoxydodecane (55 mmoles). The crude reaction mixture was heated to 100° C. for 8 hours and cooled to 20° C.

The N-(2'-hydroxydodecyl) L-histidinate of potassium was obtained at a yield of 62%.

By way of comparison, this test was repeated without the phase transfer catalyst. No condensation product was formed. Two limpid phases were observed, one containing the epoxyalkane and the other containing the amino acid.

EXAMPLE 8

In a reactor identical to that of Example 1, there was introduced under agitation 3.03 g of potassium hydroxide in tablets (54 mmoles) and 10 ml of distilled water. The reaction mixture was cooled to 5° C. and there was added, in fractions, 7.15 g of L-asparagine (54 mmoles). The mixture was agitated for 15 minutes while allowing the temperature to climb to 20° C. There was then added 0.3 g of ALIQUAT®336 (4% mass/mass of L-asparagine) and the mixture was again agitated at 500 rpm for 15 minutes at 20° C. There was then added 9.82 g of epoxydodecane (54 mmoles). The crude reaction mixture was heated to 100° C. for 8 hours, and then cooled to 20° C.

The N-(2'-hydroxydodecyl) L-asparaginate of potassium was obtained with a yield of 64%.

By way of comparison, this test was reproduced without the phase transfer catalyst. No condensation product was formed. Two limpid phases were observed, one containing the epoxyalkane and the other the amino acid.

EXAMPLE 9

In a reactor identical to that of Example 1, there was introduced under agitation 1.88 g of potassium hydroxide in tablets (34 mmoles) and 10 ml of distilled water. The reaction mixture was cooled to 5° C. and there was added in fractions, 5.60 g of D-L-phenylalanine (34 mmoles). The mixture was agitated for 15 minutes while allowing the temperature to climb to 20° C. There was then added 0.3 g of ALIQUAT®336 (5% mass/mass of D,L-phenylalanine) and the mixture was once again agitated at 500 rpm for 15 minutes at 20° C. There was then added 6.30 g of epoxydodecane (34 mmoles). The crude reaction mixture of heated to 100° C. for 5 hours 30 and cooled to 20° C.

The N-(2'-hydroxydodecyl) D,L-phenylalaninate of potassium was obtained with a yield of 96%.

By way of comparison, this test was reproduced without the phase transfer catalyst. The finished product was obtained with 77% yield.

EXAMPLE 10

In a reactor identical to that of Example 1, there was introduced under agitation 1.88 g of potassium hydroxide in tablets (34 mmoles) and 10 ml of distilled water. The reaction mixture was cooled to 5° C. and there was added, in fractions, 5.60 g of D,L-phenylalanine (34 mmoles). The mixture was agitated for 15 minutes while allowing the temperature to climb to 20° C. There was added 0.3 g of ALIQUAT®336 (5% mass/mass of D,L-phenylalanine) and the mixture was once again agitated at 500 rpm for 15 minutes at 20° C. There was then added 9.93 g of epoxyhexadecane (34 mmoles of hexadecane oxide calculated starting from the value of the index of oxiraine from the starting reactant). The crude reaction mixture was heated to 100° C. for 3 hours, (the medium becoming solid), then cooled to 20° C.

The N-(2'-hydroxyhexadecyl) D,L-phenylalaninate of potassium was obtained with a yield of 96%.

EXAMPLE 11

In a 100 ml reactor identical to that described in Example 1, there was introduced 3.20 g of N-methylglucamine (16 mmoles), 10 ml of distilled water and 0.1 g of ALIQUAT®336 (3% mass/mass of N-methylglucamine). The mixture was agitated at 500 rpm for 15 minutes at 20° C. There was then added 5.0 g of epoxyhexadecane (16 mmoles of hexadecane oxide calculated starting from the value of the index of oxirane of the starting reactant). The crude reaction mixture was heated to 100° C. for 5 hours and cooled to 20° C.

The N-(2'-hydroxyhexadecyl) methylglucamine was obtained with a yield of 95%.

By way of comparison, this test was reproduced without the phase transfer catalyst. The finished product was obtained with a 79% yield.

Although only preferred embodiments of the invention are specifically illustrated and described above, it will be appreciated that many modifications and variations of the present invention are possible in light of the above teachings and within the purview of the appended claims without departing from the spirit and intended scope of the invention.

What is claimed is:

1. A process for the preparation of a hydroxylated secondary or tertiary amine compound having a hydroxyl group β to the amine group comprising reacting a primary or secondary amine compound with an epoxy compound in the presence of a phase transfer catalyst and in the absence of an organic solvent.

2. The process according to claim 1 further comprising the step of separating the hydroxylated secondary or tertiary amine compound formed from said phase transfer catalyst.

3. The process according to claim 1 wherein the primary or secondary amine compound is a carboxyamino compound having one or two carboxylic groups in a free or salt form.

4. The process according to claim 3 wherein the carboxyamino compound is an amino acid, an oligopeptide, a peptide, an N-acylated amino acid or a heterocyclic compound comprising at least one nitrogen atom as a heteroatom and at least one carboxylic group.

5. The process according to claim 4 wherein the carboxyamino compound is an α-amino acid.

6. The process according to claim 5 wherein said α-amino acid is sarcosine, proline, threonine, histidine, asparagine, valine, phenylalanine, leucine, isoleucine, methionine, tryptophane, lysine, alanine, glummic acid, glycine, serine, tyrosine, glutamine, cysteine, cystine, aspartic acid, arginine, hydroxyproline, hydroxylysine or mixtures of these α-amino acids.

7. The process according to claim 1 wherein said primary or secondary amine is chitine or a compound of formula (I):

R—NH—G  (I)

in which R is hydrogen or a $C_1$–$C_{20}$ alkyl radical and G is a monosaccharide, a disaccharide or a polysaccharide or of hexitol.

8. The process according to claim 7 wherein R is hydrogen or a $C_1$–$C_4$ alkyl radical and G is glucose or sorbitol.

9. The process according to claim 1 wherein said compound including an epoxy function is a compound of the formula (II):

in which the substituents $R_1$, $R_2$, $R_3$ and $R_4$, which may be identical or different, represent (i) hydrogen, (ii) a group $R_5[(CH_2)_sX]_t$, wherein $R_5$ is a linear or branched, saturated or unsaturated aliphatic radical having from 1 to 30 carbon atoms, a cycloaliphatic radical having from 3 to 12 carbon atoms or an aryl radical, $R_5$ optionally having one to three hydroxyl or amine groups, or (iii) a group $R_6COOR_7$, wherein $R_6$ is a $C_1$–$C_{10}$ alkylene radical or $R_6$ represents a covalent bond and $R_7$ is H or a saturated or unsaturated, linear or branched aliphatic radical having from 1 to 30 carbon atoms, X is oxygen or sulfur, s is equal to 0 or ranges between 1 and 4 and t is equal to 0 or ranges between 1 and 20, with the proviso that at least one of $R_1$, $R_2$, $R_3$ and $R_4$ is different from hydrogen.

10. The process according to claim 9 wherein three of the substituents $R_1$, $R_2$, $R_3$ and $R_4$ represent hydrogen, the fourth substituent being different from hydrogen.

11. The process according to claim 10 wherein said substituent which is different from hydrogen is a $C_1$–$C_{20}$ alkyl radical.

12. The process according to claim 11 wherein said substituent which is different from hydrogen is a $C_8$–$C_{14}$ radical.

13. The process according to claim 1 wherein said phase transfer catalyst is a quaternary ammonium compound.

14. The process according to claim 13 wherein said quaternary ammonium compound is a quaternary ammonium halide compound.

15. The process according to claim 14 wherein said quaternary ammonium halide compound is a bromide or chloride of tetraalkylammonium or of trialkylarylammonium.

16. The process according to claim 15 wherein said phase transfer catalyst is an organic compound comprising a phosphonium group.

17. The process according to claim 1 wherein the primary or secondary amine compound which is reacted with the epoxy compound is in an aqueous solution.

18. The process according to claim 1 wherein the epoxy compound and the primary or secondary amine compound are present in a molar ratio which ranges between about 0.5 and about 10.

19. The process according to claim 18 wherein the molar ratio ranges between about 0.8 and about 1.20.

20. The process according to claim 1 wherein the epoxy compound and the primary or secondary amine compound are reacted at a temperature greater than about 95° C.

21. The process according to claim 20 wherein the epoxy compound and the primary or secondary amine are reacted at a temperature ranging between about 95° and about 160° C.

22. The process according to claim 12 wherein the epoxy compound and the primary or secondary amine are reacted at a temperature ranging between about 95° and about 125° C.

23. A process for the preparation of a hydroxylated secondary or tertiary amine compound having a hydroxyl group β to the amine group comprising reacting a primary or secondary amine compound having at least one oxygen-containing compound, in free form, selected from the group consisting of —COO⁻, —SO₃⁻, —SO₄⁻², HPO₄⁻ and —PO₃⁻² with an epoxy compound in the presence of:

(i) a phase transfer catalyst; and
(ii) a mineral base, and in the absence of an organic solvent.

24. The process according to claim 23 wherein the mineral base is LiOH, NaOH, KOH, Na₂CO₃, NaHCO₃, KHCO₃, K₂CO₃ or NH₄OH.

25. The process according to claim 23 wherein the molar ratio of the primary or secondary amine to the mineral base is between about 0.5 and about 5.

26. The process according to claim 25 wherein the molar ratio of the primary or secondary amine to the mineral base is about 1.

27. A composition comprising:

(i) at least one hydroxylated secondary or tertiary amine compound having a hydroxyl group β to the amine group; and
(ii) a phase transfer catalyst, said composition being free of organic solvents.

28. The composition according to claim 27 which is free of alcohols and ketones.

29. The composition according to claim 27 wherein said hydroxylated compound is a compound of formula (III):

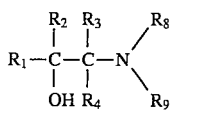

a compound of formula (IV):

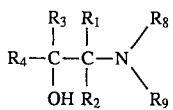

or a mixture of compounds of formulas (III) and (IV), in which R₁, R₂, R₃ and R₄, which may be identical or different, represent (i) hydrogen, (ii) a group R₅[(CH₂)ₛX]ₜ, wherein R₅ is a linear or branched, saturated or unsaturated aliphatic radical having from 1 to 30 carbon atoms, a cycloaliphatic radical having from 3 to 12 carbon atoms or an aryl radical, R₅ optionally having one to three hydroxyl or amine groups, or (iii) a group R₆COOR₇, wherein R₆ is a C₁–C₁₀ alkylene radical or R₆ represents a covalent bond and R₇ is H or a saturated or unsaturated, linear or branched aliphatic radical having from 1 to 30 carbon atoms, X is oxygen or sulfur, s is equal to 0 or ranges between 1 and 4 and t is equal to 0 or ranges between 1 and 20, with the proviso that in the formula (III), one of R₁ or R₂ is other than hydrogen and that in the formula (IV), one of R₃ or R₄ is other than hydrogen, R₈ and R₉ which are identical or different are:
one of the meanings of R₁ as defined above
a group R₁₀–ZM, where R₁₀ is a linear or branched, saturated or unsaturated aliphatic radical or an aryl radical, Z is an oxygen-containing group capable of forming a salt and M is an ion,
a monosaccharide, a disaccharide, a polysaccharide or hexitol,
a group

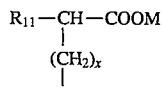

where R₁₁ is the radical of an amino acid, an oligopeptide or a peptide, M has the meaning given above and x is 0 or an integer ranging between 1 and 5 or R₈ and R₉ together with the nitrogen atom to which they are bound, form a monocyclic or polycyclic heterocycle having from 3 to 14 carbon atoms, wherein R₈ and R₉ are not simultaneously hydrogen.

30. The composition according to claim 29 wherein Z is —COO³¹, —SO₄⁻², —SO₃⁻, HPO₄⁻ or —PO₃⁻².

31. The composition according to claim 29 wherein M is NH₄⁺ or a cation of an alkali or alkaline earth metal.

32. The composition according to claim 29 wherein R₈ and R₉ further include 1 to 3 additional heteroatoms chosen among O, S and N.

33. The composition according to claim 29 wherein said heterocycle is substituted by 1 or 3 carboxylic or hydroxyl groups or both.

34. The composition according to claim 27 wherein said phase transfer catalyst is a quaternary ammonium compound.

35. The composition of claim 34 wherein said quaternary ammonium compound is a quaternary ammonium halide.

* * * * *